US006835364B2

(12) United States Patent
Stamires et al.

(10) Patent No.: US 6,835,364 B2
(45) Date of Patent: Dec. 28, 2004

(54) QUASI-CRYSTALLINE CARBOXYLATES

(75) Inventors: Dennis Stamires, Newport Beach, CA (US); Thomas Joseph Pinnavaia, East Lansing, MI (US); Michael Brady, Studio City, CA (US)

(73) Assignee: Akzo Nobel N.V., Arnhem (NL)

( * ) Notice: Subject to any disclaimer, the term of this patent is extended or adjusted under 35 U.S.C. 154(b) by 254 days.

(21) Appl. No.: 10/066,079

(22) Filed: Jan. 31, 2002

(65) Prior Publication Data

US 2002/0168313 A1 Nov. 14, 2002

Related U.S. Application Data

(60) Provisional application No. 60/267,478, filed on Feb. 9, 2001.

(30) Foreign Application Priority Data

Mar. 5, 2001 (EP) ............................................. 01200833

(51) Int. Cl.[7] .............................. C01B 3/30; C01F 7/02
(52) U.S. Cl. ................................................. 423/420.2
(58) Field of Search ............................. 423/420.2, 593, 423/625, 628, 635, 636; 502/80, 84

(56) References Cited

U.S. PATENT DOCUMENTS

| 4,946,581 | A | 8/1990 | Van Broekhoven ......... 208/120 |
| 4,952,382 | A | 8/1990 | Van Broekhoven ......... 423/244 |
| 5,108,979 | A | 4/1992 | Magnabosco et al. ...... 502/304 |
| 5,142,077 | A | 8/1992 | Martin et al. .................. 554/76 |
| 6,171,991 | B1 | 1/2001 | Stamires et al. ............ 501/141 |

FOREIGN PATENT DOCUMENTS

| EP | 0 573 610 B1 | 12/1993 | ............ B01J/21/04 |
| WO | 96/23611 | 8/1996 | ............ B22D/1/01 |
| WO | 96/29282 | 9/1996 | ........... C01B/31/30 |
| WO | 99/41196 | 8/1999 | ............. C01F/7/00 |

OTHER PUBLICATIONS

*Catalysis Today,*; Hydrotalcite–Type Anionic Clays: Preparation, Properties, and Applications. 11 (1991) pp. 173–301; Cavani et al.

Anionic Clays: Trends in Pillaring Chemistry. Synthesis in Microporous Solids; 2 (1992) pp. 108–169; Roy et al.

Helv. Chim. Acta, 25, (1942) pp. 106–137; Von Feitknecht.

Helv. Chim. Acta, 25, (1942) pp. 555–569; Von Feitknecht.

*Journal of American Ceramic Society*; Studies on 4CaO–$Al_2O_3 \cdot 13H_2O$ and the Related Natural Mineral Hydrocalumite. (1959) vol. 42 No. 3; pp. 121–126; Buttler et al.

*Chemistry Letters*; Synthesis of New Hydrotalcite–Like Compounds and Their Physico–Chemical Properties. Miyata et al.; pp. 843–848 (1973).

(List continued on next page.)

*Primary Examiner*—Stanley S. Silverman
*Assistant Examiner*—Maribel Medina
(74) *Attorney, Agent, or Firm*—Louis A. Morris

(57) ABSTRACT

The present invention provides new compositions of matter, referred to as quasi-crystalline carboxylates (QCCs), their preparation and use. The materials comprise a quasi-crystalline hydrated magnesium-aluminium hydroxy carboxylate and are characterised by the presence of at least a strong reflection in the powder X-ray diffraction pattern at a basal spacing in the range of 5 to 15 Å. The invention further relates to a process for preparing the QCCs, Mg—Al solid solutions and anionic clays under acidic conditions. The QCC is prepared by aging an acidic mixture of a magnesium carboxylate and an aluminium source. Calcination of the QCC results in a Mg—Al solid solution; rehydration of this solid solution gives an anionic clay.

18 Claims, 3 Drawing Sheets

OTHER PUBLICATIONS

*Clays and Clay Minerals*; The Synthesis of Hydrotalcite–Like Compounds and Their Structures and Physico–Chemical Properties–I: The Systems . . . ; Miyata et al. vol. 23 (1975) pp. 369–375.

*Clays and Clay Minerals*; Physico–Chemical Properties of Synthetic Hydrotalcites in Relation to Composition Miyata et al.; vol. 28, No. 1, (1980) pp. 50–56.

*Clays and Clay Minerals*; Syntheses of Disordered and Al–Rich Hydrotalcite–Like Compounds. Pausch et al.; vol. 34 No. 5; (1986) pp. 507–510.

*Materials Chemistry and Physics*, Textural Properties of Hydrotalcite–Like Compounds . . . Ulibarri et al. vol. 14 (1986) pp. 569–579.

European Search Report, for EP 01 20 0833, dated: Jul. 9, 2001.

US 6,835,364 B2

QUASI-CRYSTALLINE CARBOXYLATES

CROSS REFERENCE TO RELATED APPLICATIONS

This application claims priority from Provisional Application No. 60/267,478, filed Feb. 9, 2001, and from European Patent Application No. 01200833.0, filed Mar. 5, 2001, both applications being incorporated herein in their entirety.

FIELD OF THE INVENTION

The present invention relates to a composition comprising a quasi-crystalline hydrated magnesium-aluminium hydroxy carboxylate, its preparation and use in catalyst compositions. The invention also relates to the preparation of magnesium-aluminium solid solutions and anionic clays by using the carboxylate compositions as intermediate.

BACKGROUND OF THE INVENTION

A variety of terms are used to describe the material that is referred to in this specification as an anionic clay. Hydrotalcite-like and layered double hydroxide is interchangeably used by those skilled in the art. In this specification we refer to these materials as anionic clays, comprising within that term hydrotalcite-like and layered double hydroxide materials.

Anionic clays have many applications. These include but are not restricted to: catalysts, adsorbents, drilling muds, catalyst supports and carriers, extenders and applications in the medical field. In particular Van Broekhoven (U.S. Pat. Nos. 4,956,581 and 4,952,382) has described their use in $SO_x$ abatement chemistry.

The preparation of anionic clays has been described in many prior art publications. Articles relating to anionic clays include:
*Helv. Chim. Acta*, 25, 106–137 and 555–569 (1942)
*J. Am. Ceram. Soc.*, 42, no. 3, 121 (1959)
*Chemistry Letters* (Japan), 843 (1973)
*Clays and Clay Minerals*, 23, 369 (1975)
*Clays and Clay Minerals*, 28, 50 (1980)
*Clays and Clay Minerals*, 34, 507 (1996)
*Materials Chemistry and Physics*, 14, 569 (1986).

There is also extensive patent literature on the use of anionic clays and processes for their preparation.

Two major reviews of anionic clay chemistry were published in which the synthesis methods available for anionic clay synthesis have been summarised: F. Cavani et al "Hydrotalcite-type anionic clays: Preparation, Properties and Applications," *Catalysis Today"*, 11 (1991) Elsevier Science Publishers B. V. Amsterdam; and J P Besse and others "*Anionic clays: trends in pillary chemistry, its synthesis and microporous solids*"(1992), 2, 108, editors: M. I. Occelli, H. E. Robson, Van Nostrand Reinhold, N.Y.

Two types of anionic clay preparation are described in these reviews. The most conventional method is co-precipitation (in Besse this method is called the salt-base method) of a soluble divalent metal salt and a soluble trivalent metal salt under alkaline conditions, optionally followed by hydrothermal treatment or aging to increase the crystallite size. The second method is the salt-oxide method in which a divalent metal oxide is reacted at atmospheric pressure with a soluble trivalent metal salt, followed by aging under atmospheric pressure. This method has only been described for the use of ZnO and CuO in combination with soluble trivalent metal salts.

The prior art anionic clays are all prepared by reaction of a magnesium source and an aluminium source under basic conditions, most typically at pH values in the range 8–10 and above. The basic reaction environment, however, leads to corrosion of equipment and limits the processing conditions of their preparation and any subsequent reaction. It is therefore an object of this invention to prepare anionic clays in mildly acidic environment.

In the above mentioned reviews the authors state that a characteristic of anionic clays is that mild calcination at 500° C. results in the formation of a disordered MgO-like product. Said disordered MgO-like product is distinguishable from spinel (which results upon severe calcination) and from anionic clays. In this specification we refer to said disordered MgO-like materials as Mg—Al solid solutions. In contrast to spinel, which is a stable, irreversible phase, these Mg—Al solid solutions contain a well-known memory effect whereby the exposure to water of such calcined materials results in the reformation of the anionic clay structure. These solid solutions are the active $SO_x$ adsorbers under FCC regenerator conditions. Like anionic clays, prior art Mg—Al solid solutions are prepared under basic conditions.

The production of spinel at acidic conditions is disclosed in EP 0 573 610. The disclosed process consists of rapidly drying an acidic slurry of a magnesium and an aluminium compound, followed by calcination.

A further object of the present invention is a new process for the production of anionic clays.

SUMMARY OF THE INVENTION

In one embodiment, the present invention comprises new compositions of matter, referred to as quasi-crystalline carboxylates (QCCs), which are quasi-crystalline hydrated magnesium-aluminium hydroxy carboxylates. These quasi-crystalline carboxylates are characterised at least by a strong reflection in the powder X-ray diffraction pattern at a basal spacing in the range of 5 to 15 Å. The QCCs according to the invention may optionally comprise a hydrated magnesium hydroxy carboxylate, a hydrated aluminium hydroxy carboxylate and/or aluminium oxide.

In another embodiment, the invention comprises a process for preparing these QCCs, a process to prepare from them Mg—Al solid solutions, and a process to prepare from the latter anionic clays. The process to prepare QCCs comprises aging of an acidic mixture comprising a magnesium carboxylate and an aluminium source. Calcination of the QCC results in a Mg—Al solid solution, and rehydration of the solid solution gives an anionic clay.

Other embodiments of the invention relate to use of the QCCs of the invention, such as in a catalyst composition.

Figure 1:
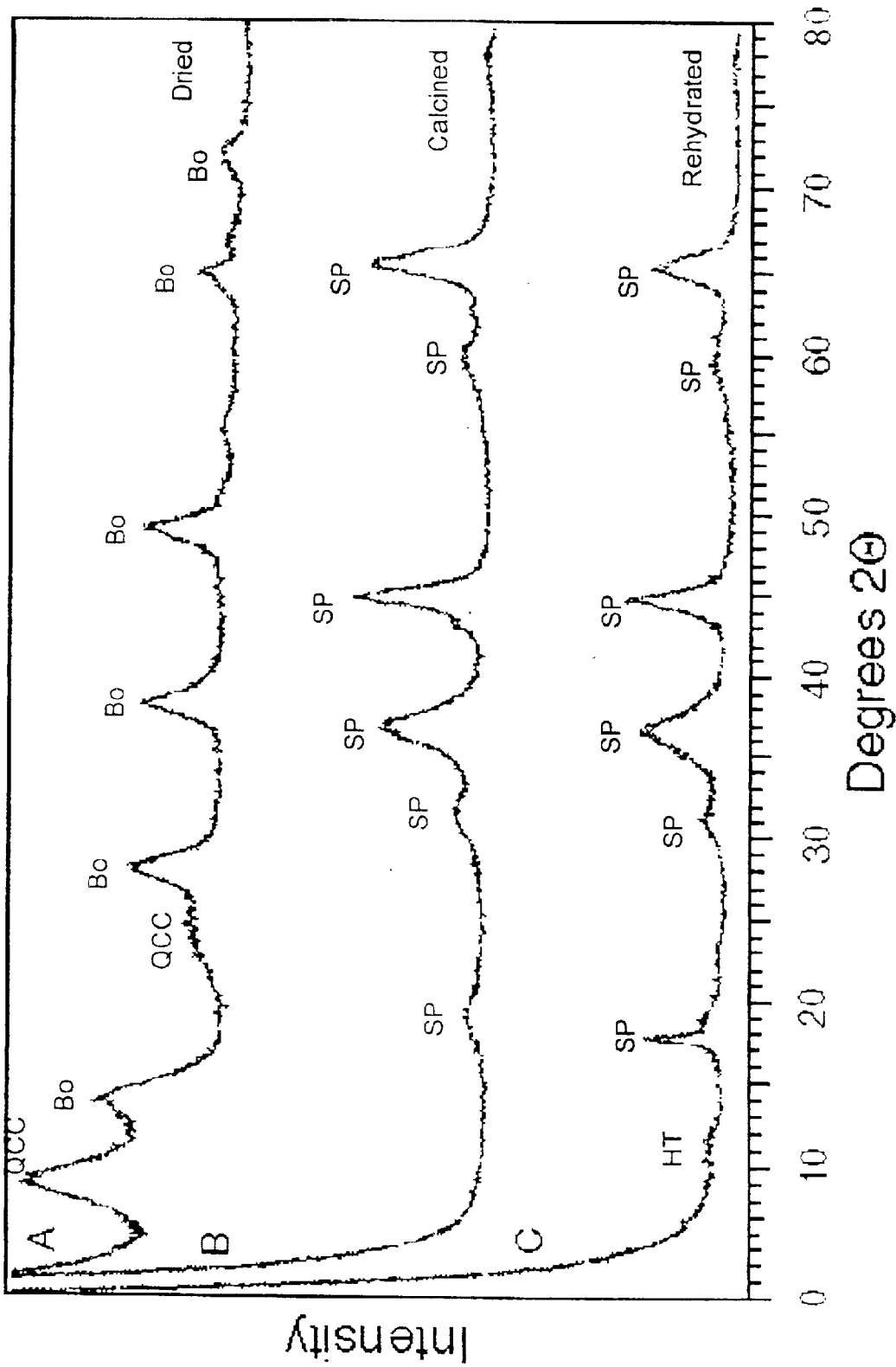
FIG. 1 shows the PXRD patterns of a QCC with a Mg/Al ratio of 0.5, its calcined and subsequently rehydrated form. The aluminium source is a peptizable pseudoboehmite; the carboxylate is acetate.

In these figures QCC stands for quasi-crystalline hydrated magnesium-aluminium hydroxy carboxylate, SP for spinel, Mg/AlO for magnesium-aluminium solid solution, HT for anionic clay and Bo for pseudoboehmite.

DETAILED DESCRIPTION OF THE INVENTION

The process of EP 0 573 610 differs from that of the present invention in several ways. First, the products after calcination are different. The product of the present invention is a solid solution which can be rehydrated to an anionic clay; EP 0 573 610 produces spinels, which cannot be rehydrated to anionic clays. Secondly, the present invention is related to quasi-crystalline carboxylates. These materials are not formed as intermediates in the process according to EP 0 573 610, because no aging step is performed. Aging is essential for the formation of the quasi-crystalline carboxylates according to the present invention.

Carboxylate salts of electropositive metals such as magnesium can be readily prepared by reaction of the oxide with an aqueous solution of the free acid form of the desired carboxylate. Thus, magnesium acetate can be readily obtained by the reaction of magnesium oxide, i.e. magnesia, with acetic acid in aqueous solution. In this reaction magnesium hydroxide may be substituted for magnesium oxide as the source of magnesium.

Typical examples of carboxylates suitable for the formation of the quasi-crystalline magnesium-aluminium carboxylates according to the invention include monocarboxylates, such as acetate, formate, and propionate, and dicarboxylates, such as oxalate, malonate, and succinate. Particularly preferred carboxylates are acetate and formate. Formic acid is cheap and reacts readily with magnesium oxide to form magnesium formate. However, the solubility and reactivity of magnesium formate towards active alumina are lower than those of magnesium acetate.

Aluminium salts, aluminium hydroxides, aluminium oxides, and combinations thereof can be used as aluminium source for the preparation of the quasi-crystalline magnesium-aluminium carboxylates according to the present invention. Suitable aluminium salts include aluminium nitrate, aluminium chloride, aluminium carboxylates, and mixtures thereof. Preferred aluminium salts are aluminium nitrate and aluminium carboxylates. The nitrate and carboxylate anions will be decomposed upon calcination, making washing steps redundant.

Aluminium oxides, so-called aluminas, that can be used include amorphous forms of hydrous aluminium oxides, which are also known as active aluminas, transition aluminas, and mixtures thereof. Active aluminas, which include aluminium hydroxide gel powders, are commercially available reagents. A very important transition alumina is pseudoboehmite. This is a commercially available hydrous alumina with an idealised composition of AlO(OH). Pseudoboehmite exhibits a powder X-ray diffraction (PXRD) pattern with peaks at the positions found for boehmite, but owing to the presence of a small particle size and structural defects, the diffraction peaks are very broad. Pseudoboehmites may or may not be peptizable in acidic solution. One commercially available pseudoboehmite that is peptizable is produced by the Vista Chemical Company under the name Catapal A®. Non-peptizable pseudoboehmites are supplied by the LaRoche Chemical Company, under the name Versal-250®, and Condea Chemie, under the name P-200®.

The aluminium source, the magnesium carboxylate, and water are fed to a reactor and the resulting suspension is aged to obtain the quasi-crystalline carboxylate according to the invention. The reactor may be equipped with stirrers, baffles etcetera to ensure homogeneous mixing of the reactants. The aqueous suspension in the reactor may be obtained by either adding slurries or solutions of the starting materials, either combined or separate, to the reactor or adding the magnesium carboxylate to a slurry of the aluminium source or vice versa and adding the resulting slurry to the reactor. It is possible to treat, for instance the aluminium source slurry at elevated temperature and then add either the magnesium carboxylate per se, or add the magnesium carboxylate in a solution either to the reactor or the aluminium source slurry. Especially when using metal sources like oxides or hydroxides, it is usually advisable to mill the metal source before use. Preferably, both the aluminium source and the magnesium carboxylate are milled before use. When wet milling is used, the slurry containing both the aluminium source and the magnesium carboxylate may be wet milled, for instance in a ball mill.

The reaction takes place during aging. Within the context of this description aging means treatment at ambient or at elevated temperature and at atmospheric or elevated pressure for a time period in the range of 15 minutes to 60 hours. The aging time depends on the temperature and the activity of the starting materials. Usually, a temperature between room temperature and 300° C. is used at or above atmospheric pressure. It is preferred to carry out the process at temperatures above 50° C. rather than at room temperature, because this results in compositions with sharper peaks in the X-ray diffraction pattern than QCCs obtained at room temperature. The reactor may be heated by any suitable heating source such as a furnace, microwave, infrared sources, heating jackets (either electrical or with a heating fluid), and lamps. Because of its simplicity, the process is particularly suitable to be carried out in a continuous mode.

Aging may be conducted hydrothermally. Within the context of this description hydrothermal means in the presence of water (or steam) at a temperature above 100° C. at elevated pressure, e.g autogenous pressure. Hydrothermal treatment is particularly advantageous, because this is faster and a higher conversion is obtained.

In a further embodiment of the invention, the process is conducted in a multi-step fashion, e.g. a slurry of aluminium source and magnesium carboxylate is aged thermally in a first reactor at a mild temperature, followed by a hydrothermal treatment in a second reactor or vice versa. If desired a previously formed QCC may be added to the reactor. Said QCC may be recycled QCC from the reaction mixture or a QCC made separately by the invention process or some other process.

The reaction is conducted under acidic conditions, i.e. a pH in the range of 3.5 to 6.5. For the preparation of magnesium-aluminium acetates the preferred range is 5.0 to 6.0; when the carboxylate is formate the preferred range is 4.5 to 6.0. The pH is controlled by addition of acids or bases. These may be fed to the reactor or added to either the magnesium solution and/or the aluminium source before they are fed to the reactor. An example of a preferred base is an ammonium base. A preferred acid is a carboxylic acid. By using these acids or bases, no washing step is required to remove deleterious cations.

The Mg/Al molar ratio of the starting compounds is typically 0.5–5.0, and preferably 0.75–5.0, whereas the carboxylate/Mg molar ratio is preferably between 2.0 and 8.0.

The degree to which a magnesium carboxylate will react with an aluminium source depends on the nature of the carboxylate anion and on the nature of the aluminium source. In general, acetate is more reactive than formate. Active aluminas, as represented by amorphous aluminium hydroxide gel powders, are more reactive than transition aluminas, such as pseudoboehmite. The extent of the reaction depends further on the reaction conditions. For instance, hydrothermal treatments greatly facilitate the reaction. Those skilled in the art will therefore understand that the compositions obtained from the process according to the invention can be complex mixtures containing both QCC and unreacted (i.e. not reacted to QCC) reagent phases, such as alumina and magnesium carboxylate.

The QCCs according to the invention exhibit broad powder X-ray diffraction (PXRD) patterns that are distinguishable from pure carboxylate salts of magnesium and aluminium. The PXRD patterns of QCCs are also distinguishable from those of anionic clays and Al—Mg solid solutions. The strongest peak in the pattern occurs in the low 2-theta region corresponding to a basal spacing in the range of 5.0 to 15.0 Å, depending on the ratio of magnesium to aluminium used to prepare the compositions. In the absence of obscuring peaks (see below) two additional broad, but weaker reflections can be observed at basal spacings in the ranges 3.5–3.7 Å and 2.25–2.35 Å. On the basis of the broadness and limited number of diffraction lines in the PXRD-patterns, the magnesium-aluminium carboxylate compositions of the present invention are referred to as quasi-crystalline.

Depending on the aluminium reagent used to form the QCCs according to the invention, the weak PXRD reflections of the QCCs may be obscured by reflections of an unreacted alumina phase, so that only the strongest reflection may be observed.

Infrared spectra of the QCCs according to the invention exhibit a broad absorption band in the region between 3000 and 4000 $cm^{-1}$, which is assignable to the OH stretching frequency of the water molecules. This proves that the QCCs are in fact hydrated species.

The structure of the QCC and, therefore, the position of its PXRD reflection depends in part on the type of carboxylate, the aluminium source used and the water content of the QCC. For instance, magnesium-aluminium acetates dried at 120° C. show their strongest reflection in the range of 9.0 to 15.0 Å, whereas magnesium-aluminium formates dried at the same temperature exhibit the corresponding peak in the range of 5.0 to 9.0 Å. A more reactive (amorphous) alumina gives a quasi-crystalline acetate with a basal spacing near 14 Å, whereas a less reactive alumina, such as pseudoboehmite, affords a quasi-crystalline acetate with a spacing near 9.5 Å. This difference is attributed to a difference in the resulting Mg/Al ratio in the QCC.

The temperature used to dry the QCC also affects the PXRD pattern, because removal of water from the crystal lowers the d-spacing.

The QCCs according to the invention can advantageously be used for various purposes which need a reactive Mg/Al reagent or a mild base. For example, QCCs can be used as pharmaceutical anti-acids. Other examples of such applications are the use as absorbent for the purification of waste water or gaseous streams, as catalyst additive or matrix.

The QCCs according to the invention may be used directly in oven-dried or spray-dried form for the adsorption of $SO_x/NO_x$ in the regenerator section of an FCC unit. At the temperature of the regenerator, typically 700°–800° C., the QCCs according to the invention are transformed into a mixture of metal oxides. In certain applications, it may be desirable to calcine the QCCs of the present invention in order to remove carboxylate. The QCCs may be converted to magnesium-aluminium oxide compositions by calcination at temperatures in the range of 300° to 1200° C., preferably 400°–1000° C. The calcination may for instance be carried out in a rotary kiln. Alternatively, the QCC may be flash calcined. The preferred range for removing acetate and formate is 700°–800° C. Calcination at 700°–800° C. of QCCs with Mg/Al ratios in the range 0.5–0.75 leads to products which consist primarily of spinel. As the Mg/Al ratio is increased beyond 0.75, the calcined products comprise, in addition to spinel, magnesium oxide and magnesium-aluminium oxide solid solutions with a magnesium oxide lattice structure. This invention therefore relates also to the preparation of Mg—Al solid solutions by calcination of QCCs.

The magnesium oxide and the solid solution phase can be distinguished by rehydration of the calcined product in aqueous suspension. The magnesium oxide component reacts very slowly with water to form brucite, i.e. $Mg(OH)_2$. In contrast, rehydration of the solid solution results in the formation of an anionic clay within 24 hours. Within this period, magnesium oxide remains largely unreacted.

Therefore, this invention also relates to a process for the preparation of anionic clays from QCCs. The anionic clays formed by this method have a layered structure corresponding to the general formula:

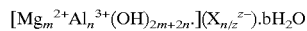

$[Mg_m^{2+}Al_n^{3+}(OH)_{2m+2n}\cdot](X_{n/z}^{z-})\cdot bH_2O$ wherein m and n have a value such that m/n=1 to 10, preferably 1 to 6, and b has a value in the range from 0 to 10, generally a value of 2 to 6 and often a value of about 4. X may be $CO_3^{2-}$, $OH^-$, or any other anion normally present in the interlayers of anionic clays. It is more preferred that m/n should have a value of 2 to 4, more particularly a value close to 3. If the reaction mixture is free of carbon dioxide the product formed by rehydration of the solid solution is a meixnerite-like anionic clay.

The PXRD patterns of the rehydrated calcined QCCs according to the invention comprise peaks characteristic of anionic clays with basal spacings in the range 7.0–9.5 Å, the exact spacing depending on the Mg/Al ratio and the degree of hydration. Beside these peaks, the rehydrated samples may also comprise peaks indicative of alumina (e.g. pseudoboehmite), spinel, unreacted magnesium oxide and/or brucite.

The rehydration to form anionic clays can be performed by contacting the calcined material in and with water for 1–24 hours at 65°–85° C. Preferably, the slurry is stirred and has a solids content in the range of 1 to 50 wt %. During this rehydration additives (see below) can be added.

If desired, the anionic clay may be subjected to ion-exchange. Upon ion-exchange the interlayer charge-balancing anions are replaced with other anions. Examples of suitable anions are carbonates, bicarbonates, nitrates, chlorides, sulphates, bisulphates, vanadates, tungstates, borates, phosphates, pillaring anions such as $HVO_4^-$, $V_2O_7^{4-}$, $HV_2O_{12}^{4-}$, $V_3O_9^{3-}$, $V_{10}O_{28}^{6-}$, $Mo_7O_{24}^{6-}$, $PW_{12}O_{40}^{3-}$, $B(OH)_4^-$, $B_4O_5(OH)_4^{2-}$, $[B_3O_3(OH)_4]^-$, $[B_3O_3(OH)_5]^{2-}$ $HBO_4^{2-}$, $HGaO_3^{2-}$, $CrO_4^{2-}$, and for Keggin-ions, formates, acetate and mixtures thereof. Said ion-exchange can be conducted before or after drying the anionic clay formed by rehydration.

For some applications it is desirable to have additives, more in particular metal compounds and/or non-metal compounds, such as compounds of rare earth metals (for example Ce, La), Si, P, B, group VI, group VIII, alkaline earth (for instance Ca and Ba) and/or transition metals (for example W, V, Mn, Fe, Ti, Zr, Cu, Ni, Zn, Mo, Sn), present in the compositions according to the invention, that is, in the QCCs, the calcined products or the rehydrated products. The additives, or their precursors, can be deposited on the compositions, they can be added either to the magnesium carboxylate starting material or the aluminium source before adding to the reactor, or they can be added to the reactor separately. Suitable sources of metal compounds or non-metal compounds are oxides, halides such as chlorides, nitrates, and phosphates.

The compositions according to the invention, i.e. the QCC, the calcined product or the rehydrated product, may be spray-dried, extruded or beaded to form shaped bodies. Spray-drying results in the formation of microspheres. This shaping can be performed after, before or, in the case of a multi-step process, during the aging step. If unreacted alumina is present in the QCC, the calcined product, or the rehydrated product, it acts as a binder.

Suitable shaping methods include spray-drying, pelletizing, extrusion (optionally combined with kneading), beading, or any other conventional shaping method used in the catalyst and absorbent fields or combinations thereof. The amount of liquid present in the slurry used for shaping should be adapted to the specific shaping step to be conducted. To this end one may partially remove the liquid used in the slurry and/or add an additional or another liquid, and/or change the pH of the precursor mixture to make the slurry gellable and thus suitable for shaping. Various additives commonly used in the various shaping methods, such as extrusion additives, may be added to the precursor mixture used for shaping.

The incorporation of a $SO_x/NO_x$ absorbant into a FCC process for petroleum refining can be facilitated by combining the absorbant as part of the FCC catalyst particle. The present invention also contemplates an FCC catalyst comprising a quasi-crystalline magnesium-aluminium hydroxy carboxylate according to the present invention, its calcined form and/or the rehydrated form of the latter.

The invention is illustrated by the following Examples.

EXAMPLES

Example 1

A magnesium acetate solution was prepared as follows. Glacial acetic acid (996 g) was added to de-ionized water (1108 g). To this solution 335 g MgO (Spectrum Chemical Company; Hoavy USP powder; MA125) was slowly added, while stirring, until all of the MgO had dissolved producing a solution with pH 5.45.

Example 2

An alumina sol was prepared by adding 50.0 g of Catapal A® to a mixture of 3.45 g glacial acetic acid and 245.0 g de-ionized water and mixing in a Waring blender at high speed for 15 minutes. To the resulting mixture 103.4 g of the magnesium acetate solution of Example 1 was added. The resulting mixture was mixed in the blender for 20 minutes, producing a gel with a pH of 5.53 and a Mg/Al molar ratio of 0.5. The gel was aged at 80° C. for 27 hours in a sealed container. The product was dried overnight in an oven at 100° C. and ground to fine powder.

FIG. 1 shows the PXRD pattern of the sample, obtained by using CuK-alpha radiation with a wavelength of 1.5418 Å. This pattern contains reflections characteristic for unreacted pseudoboehmite and two reflections of the QCC at about 9° and 24° theta, corresponding to spacings of around 11.1 and 3.7 Å. A reflection of the pseudoboehmite phase obscures the third QCC reflection near 38° two theta (2.4 Å). FIG. 1 also shows the PXRD pattern of this sample after calcination at 732° C. and after a subsequent rehydration. These patterns indicate that spinel is the main phase formed.

Example 3

Figure 2:
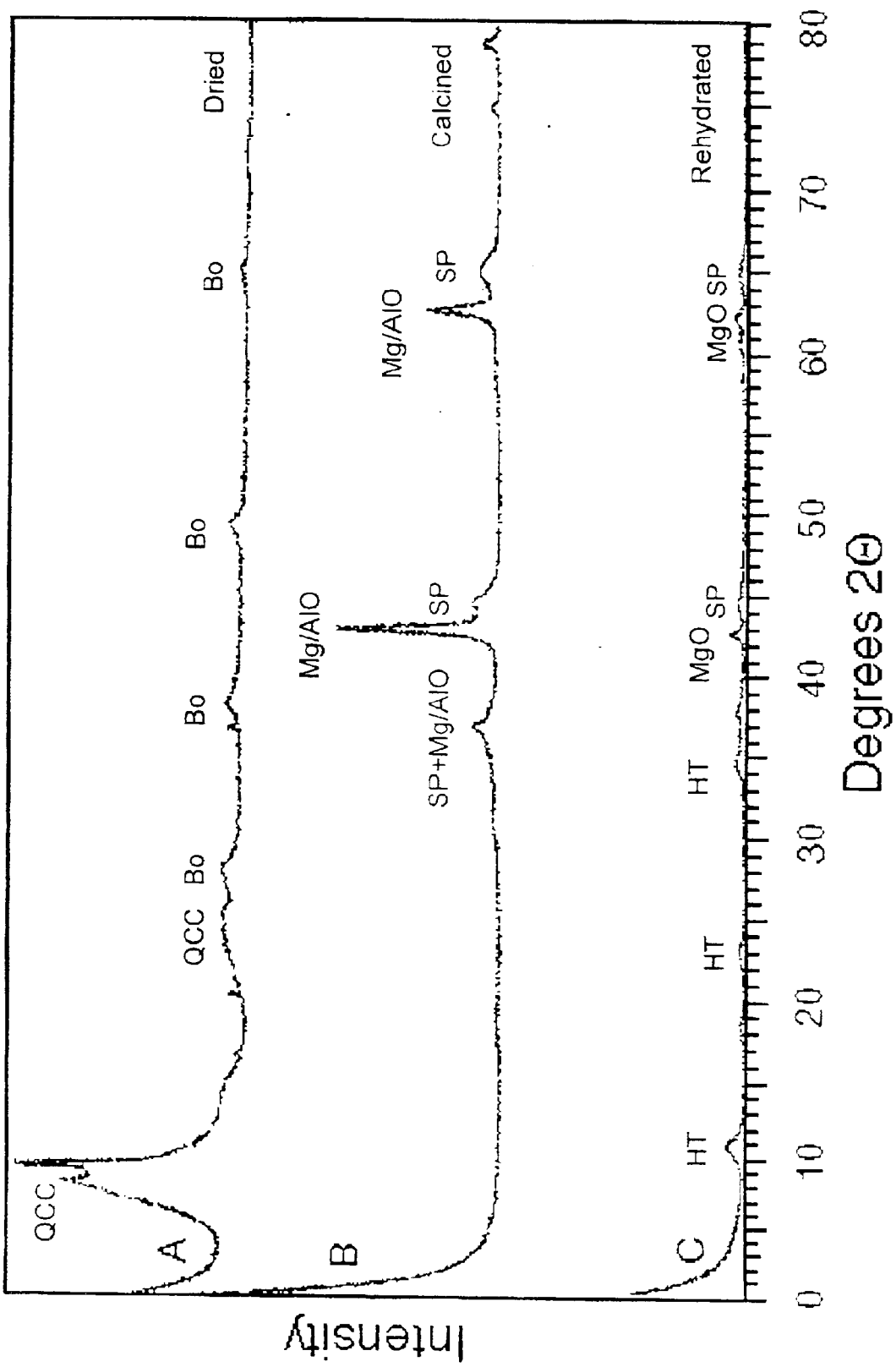
FIG. 2 shows the PXRD patterns of a QCC with a Mg/Al ratio of 2.0, its calcined and subsequently rehydrated form. The aluminium source is a peptizable pseudoboehmite; the carboxylate is acetate.

Example 2 was repeated, except that 413.5 g of magnesium acetate solution was used, resulting in a Mg/Al molar ratio of 2.0. The pH of the gel was 5.45. FIG. 2 shows the PXRD pattern of the product. This pattern indicates the formation of QCC and pseudoboehmite. FIG. 2 also shows the PXRD pattern of this sample after calcination at 732° C. and a subsequent rehydration. These patterns indicate that after calcination both spinel and Mg/Al solid solution are present. Upon rehydration of this calcined material the solid solution is transformed into anionic clay, brucite, and magnesium oxide.

Example 4

An alumina sol was prepared by adding 30.0 g of Catapal A® alumina to a mixture of 1.99 g glacial acetic acid and 147.0 g de-ionized water and mixing in a Waring blender at high speed for 15 minutes. To the resulting mixture, 496.2 g of the magnesium acetate solution of Example 1 was added. The resulting mixture was mixed in the blender for 20 minutes, producing a gel with a pH of 5.47 and a Mg/Al molar ratio of 4.0.

Three portions of the gel were aged under the following conditions:

Portion 1. room temperature for 29 hours
Portion 2. 80° C. for 27 hours in a sealed container
Portion 3. 175° C. at 8.2 · 10$^5$ Pa (120 psig) for 60 minutes, using a Microwave Sample Preparation System manufactured by the CEM Corporation.

For all these samples the PXRD diffraction patterns indicated the formation of QCC and pseudoboehmite.

Example 5

A dispersion of alumina was prepared by adding 66.8 g of an aluminium hydroxide gel powder (an amorphous alumina produced by the Chattem Chemicals, Inc.) to a mixture of 3.32 g glacial acetic acid and 108.9 g de-ionized water and mixing in a Waring blender at high speed for 15 minutes. To the resulting mixture, 206.8 g of the magnesium acetate solution of Example 1 was added. The resulting mixture was mixed in the blender for 20 minutes, producing a gel with a pH of 5.75 and a Mg/Al molar ratio of 1.0.

Three portions of the gel were aged under the following conditions:

Portion 1. room temperature for 29 hours
Portion 2. 80° C. for 27 hours in a sealed container
Portion 3. 175° C. at 8.2 · 10$^5$ Pa (120 psig) for 60 minutes, using a Microwave Sample Preparation System manufactured by the CEM Corporation.

The samples were dried overnight in an oven at 100° C. and ground to fine powder. For the aging carried out at room temperature (Portion 1), the three lines characteristic of the QCC phase were clearly visible, because the unreacted fraction of the aluminium source is amorphous and could not obscure these reflections.

Figure 3:
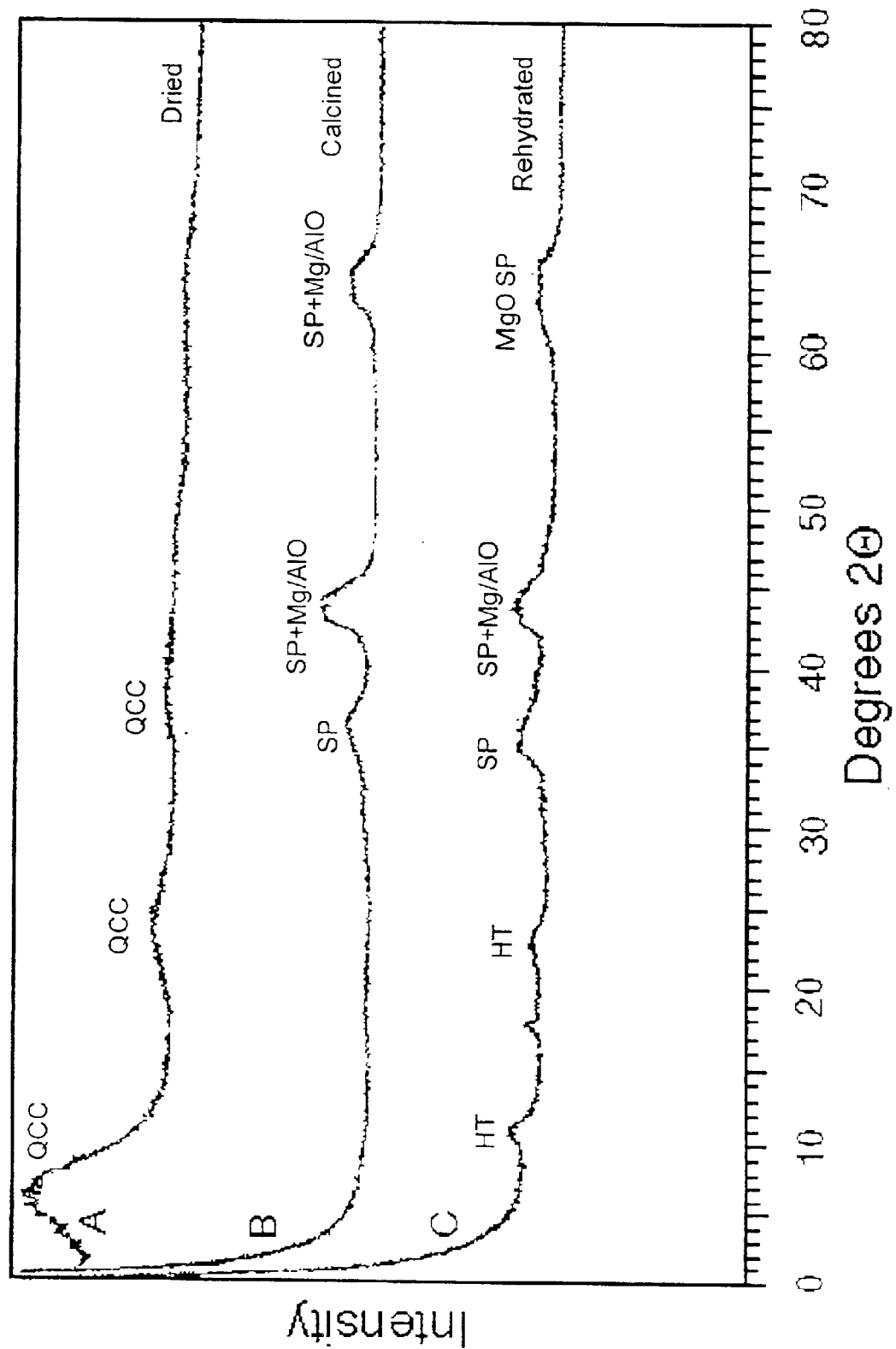
FIG. 3 shows the PXRD patterns of a QCC with a Mg/Al ratio of 3.0, its calcined and subsequently rehydrated form. The aluminium source is an aluminium hydroxide gel powder; the carboxylate is acetate.

FIG. 3 shows the PXRD pattern of the sample aged at 80° C. (Portion 2). The diffraction pattern shows the three characteristic QCC reflections. FIG. 3 also shows the PXRD patterns of this sample after calcination at 732° C. and a subsequent rehydration. These patterns indicate that after calcination both spinel and Mg/Al solid solution are present. The spinel/solid solution ratio is higher than in Example 3 (FIG. 2). Upon rehydration of the calcined material, the majority of the solid solution is transformed into anionic clay and magnesium oxide.

Similar results were obtained for the sample treated at 175° C.

Example 6

A dispersion of alumina was prepared by adding 52.5 g of a Versal-250® alumina to a mixture of 3.32 g glacial acetic acid and 123.1 g de-ionized water and mixing in a Waring blender at high speed for 15 minutes. To the resulting mixture, 206.8 g of the magnesium acetate solution of Example 1 was added. The resulting mixture was mixed in the blender for 20 minutes, producing a gel with a pH of 5.67 and a Mg/Al molar ratio of 1.0.

Three portions of the gel were aged under the following conditions:

Portion 1. room temperature for 29 hours
Portion 2. 80° C. for 27 hours in a sealed container
Portion 3. 175° C. at 8.2 · 10$^5$ Pa (120 psig) for 60 minutes, using a Microwave Sample Preparation System manufactured by the CEM Corporation.

In all cases, the PXRD patterns showed the formation of QCC and pseudoboehmite.

Example 7

An alumina sol was prepared by adding 40.0 g of Catapal A® alumina to a mixture of 3.25 g formic acid (8 wt. %) and 148.0 g de-ionized water and mixing in a Waring blender at high speed for 15 minutes. To the resulting mixture, a solution of 81.8 g of magnesium formate (ex Pfaltz & Bauer, Co) dissolved in 463.0 g de-ionized water was added. The resulting mixture was mixed in the blender for 20 minutes, producing a gel with a pH of 5.53 and a Mg/Al molar ratio of 1.0. The gel was aged at 80° C. for 48 hours in a sealed container. The product was dried overnight in an oven at 100° C. and ground to fine powder. The PXRD diffraction pattern indicated the formation of QCC and pseudoboehmite.

Example 8

Different samples were prepared by mixing aqueous solutions of magnesium acetate prepared according to Example 1 with aqueous solutions of aluminium nitrate. Each sample had a different Mg/Al ratio in the range 0.5–5.0. The samples were aged at room temperature for 27 hours and the pH was adjusted to 6.0 by using ammonium hydroxide. The resulting precipitates were collected by filtration and air-dried. PXRD indicated the formation of QCC in the precipitates formed in each of the samples.

What is claimed is:

1. A composition comprising a quasi-crystalline hydrated magnesium-aluminium hydroxy carboxylate displaying a reflection in the powder X-ray diffraction pattern in the range of 5 to 15 Å.

2. The composition of claim 1 which also comprises a hydrated magnesium hydroxy carboxylate or a hydrated aluminium hydroxy carboxylate or both a hydroxy carboxylate and a hydrated aluminium hydroxy carboxylate.

3. The composition of claim 1 which also comprises an aluminium oxide.

4. The composition of claim 1 wherein the carboxylate is acetate or formate.

5. The composition of claim 1 wherein the magnesium to aluminium molar ratio in the composition ranges from 0.5 to 5.0.

6. The composition of claim 5 wherein the magnesium to aluminium molar ratio in the composition ranges from 0.75 to 5.0.

7. A process for the preparation of the composition of claim 1 wherein a mixture of an aluminium source and a magnesium carboxylate is aged at a pH in the range of from 3.5 to 6.5.

8. The process of claim 7 wherein the magnesium carboxylate is magnesium acetate or magnesium formate.

9. The process of claim 7 wherein the aluminium source is an aluminium salt, pseudoboehmite, amorphous aluminium hydroxide gel powder, or a combination thereof.

10. The process of claim 7 wherein aging occurs under hydrothermal conditions.

11. The process of claim 7 wherein the aging is conducted in two separate steps, one under thermal and one under hydrothermal conditions.

12. The process of claim 7 wherein the process is conducted in a continuous mode.

13. A process for the preparation of a Mg—Al solid solution wherein the composition of claim 1 is calcined at a temperature in the range of 300° to 1200° C.

14. The process of claim 13 wherein said solid solution is shaped.

15. A process for the preparation of an anionic clay wherein the composition of claim 1 is calcined and the calcined product is subsequently rehydrated to obtain an anionic clay.

16. The process of claim 15 wherein said anionic clay is shaped.

17. A catalyst composition comprising the composition of claim 1.

18. A shaped composition of claim 1.

* * * * *

UNITED STATES PATENT AND TRADEMARK OFFICE
CERTIFICATE OF CORRECTION

| | |
|---|---|
| PATENT NO. | : 6,835,364 B2 |
| APPLICATION NO. | : 10/066079 |
| DATED | : December 28, 2004 |
| INVENTOR(S) | : Stamires et al. |

It is certified that error appears in the above-identified patent and that said Letters Patent is hereby corrected as shown below:

On the title page,

[*] Notice: Subject to any disclaimer, the term of this patent is extended of adjusted under 35 USC 154(b) by (254) days Delete the phrase "by 254 days" and insert -- by 324 days--

Signed and Sealed this

Twentieth Day of February, 2007

JON W. DUDAS
*Director of the United States Patent and Trademark Office*